US012678577B2

(12) United States Patent
Van Zanten et al.

(10) Patent No.: US 12,678,577 B2
(45) Date of Patent: Jul. 14, 2026

(54) CONTROLLING A RESPIRATORY SUPPORT SYSTEM

(71) Applicant: KONINKLIJKE PHILIPS N.V., Eindhoven (NL)

(72) Inventors: Joyce Van Zanten, Waalre (NL); Angela Grassi, Eindhoven (NL); Pedro Miguel Ferreira Dos Santos Da Fonseca, Antwerp (BE); Joachim Johannes Kahlert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 618 days.

(21) Appl. No.: 18/080,196

(22) Filed: Dec. 13, 2022

(65) Prior Publication Data

US 2023/0191058 A1 Jun. 22, 2023

(30) Foreign Application Priority Data

Dec. 20, 2021 (EP) ..................................... 21215920

(51) Int. Cl.
*A61M 16/00* (2006.01)
*G06T 7/70* (2017.01)
(52) U.S. Cl.
CPC ............. *A61M 16/024* (2017.08); *G06T 7/70* (2017.01); *A61M 2230/62* (2013.01); *A61M 2230/63* (2013.01); *G06T 2207/30196* (2013.01)
(58) Field of Classification Search
CPC ............ A61M 16/024; A61M 2230/62; A61M 2230/63; A61M 16/06; A61M 2016/1025;
(Continued)

(56) References Cited

U.S. PATENT DOCUMENTS

2012/0199124 A1 8/2012 Bowditch

FOREIGN PATENT DOCUMENTS

DE 20008049 U1 * 8/2000
EP 2008581 A2 12/2008
(Continued)

OTHER PUBLICATIONS

Translation DE 20008049 U1 (Year: 2008).*
(Continued)

*Primary Examiner* — Victoria Murphy
(74) *Attorney, Agent, or Firm* — Brynne J. Corcoran

(57) ABSTRACT

In an embodiment, a control system is described. The control system controls a respiratory support system for supplying therapy gas to a subject. The control system comprises processing circuitry communicatively coupled to an interface for receiving an indication of a combination of the subject's head orientation and torso orientation. The indication is based on orientation data provided by a sensing system configured to detect the subject's head orientation and torso orientation. The control system further comprises a machine-readable medium storing instructions. When executed by the processing circuitry, the instructions cause the processing circuitry to identify, from parameter information associated with each of a set of different combinations of head orientation and torso orientation, a parameter value of the therapy gas for the respiratory support system to use in supplying the therapy gas to the subject for the indicated combination of the subject's head orientation and torso orientation. The respiratory support system is caused to supply the therapy gas with the identified parameter value.

15 Claims, 3 Drawing Sheets

(58) Field of Classification Search
CPC .... A61M 2205/332; A61M 2205/3331; A61M
2205/3375; A61M 2205/3553; A61M
2205/3561; A61M 2205/3584; A61M
2205/3592; A61M 2210/06; A61M
2210/10; G06T 7/70; G06T 2207/30196;
A61B 5/4836; A61B 5/4818; A61B
5/1116; G16H 20/40
See application file for complete search history.

(56)  References Cited

FOREIGN PATENT DOCUMENTS

| WO | WO-9716216 A1 * | 5/1997 | ........ A61M 16/0051 |
|----|----------|--------|----------|
| WO | 0200283 A1 | 1/2002 | |
| WO | 2013133850 A1 | 9/2013 | |
| WO | 20140118653 A1 | 8/2014 | |

OTHER PUBLICATIONS

Van Kesteren et al; "Quantitative Effects of Trunk and Head
Position on the Apnea Hypopnea Index in Obstructive Sleep Apnea",
Sleep, vol. 34, No. 8, 2011.

* cited by examiner

300

CONTROLLING A RESPIRATORY SUPPORT SYSTEM

CROSS REFERENCE TO RELATED APPLICATION

This patent application claims the priority benefit under 35 U.S.C. § 119(e) of U.S European Application No. 21215920 filed Dec. 20, 2021, the contents of which are herein incorporated by reference.

TECHNICAL FIELD OF THE INVENTION

The invention relates to a control system, a patient support system, a method and a non-transitory machine-readable medium for controlling a respiratory support system.

BACKGROUND OF THE INVENTION

It has been demonstrated that body position (e.g., or "orientation") during sleep may affect the severity of respiratory disturbances (e.g. apnea and/or hypopnea events) in subjects with obstructive sleep apnea (OSA) and hypoventilation (shallow breathing) in obesity hypoventilation syndrome (OHS). In a large proportion of subjects, the apnea hypopnea index (AHI) is higher when lying on the back (i.e., the supine position) in comparison to the other sleeping positions (i.e., non-supine positions such as when the patient is on their side or in the prone position). In OHS, a patient's breathing may be shallower in the supine position. Hypnogram studies suggest a clustering of respiratory events correlated with changes in body position. However, in some cases there are hypnograms with this clustering of apnea/ hypopnea, but without any clear relation with the recorded body position (or sleep stage).

SUMMARY OF THE INVENTION

Certain aspects or embodiments described herein may relate to improving the delivery of therapy gas provided by respiratory support systems. Certain aspects or embodiments may address problems relating to ensuring that the therapy gas provided by such respiratory support systems meets the subject's respiratory and/or sleep needs.

In a first aspect of the invention, a control system is described. The control system is for controlling a respiratory support system for supplying therapy gas to a subject. The control system comprises processing circuitry communicatively coupled to an interface for receiving an indication of a combination of the subject's head orientation and torso orientation. The indication is based on orientation data provided by a sensing system configured to detect the subject's head orientation and torso orientation. The control system further comprises a machine-readable medium storing instructions which, when executed by the processing circuitry, cause the processing circuitry to identify a parameter value of the therapy gas for the respiratory support system to use in supplying the therapy gas to the subject for the indicated combination of the subject's head orientation and torso orientation. The parameter value is identified from parameter information associated with each of a set of different combinations of head orientation and torso orientation. The instructions further cause the processing circuitry to cause the respiratory support system to supply the therapy gas with the identified parameter value.

Some embodiments relating to the first and other aspects are described below.

In some embodiments, the indication is configured to indicate whether the subject's head orientation and torso orientation are the same or different.

In some embodiments, the indication comprises information indicative of the subject's head orientation being different to the subject's torso orientation.

In some embodiments, the head orientation is one of: a supine head orientation or non-supine head orientation. In some embodiments, the torso orientation is one of: a supine torso orientation or non-supine torso orientation.

In some embodiments, the parameter value to use is a default parameter value when the indicated combination comprises the supine head orientation and the supine torso orientation. The parameter value to use is different to the default parameter value when the indicated combination comprises at least one of: a non-supine head orientation and/or non-supine torso orientation.

In some embodiments, a first parameter value from the parameter information is associated with a first combination of the set of different combinations of head orientation and torso orientation. The first combination is where the head orientation is supine and the torso orientation is supine. Further, a second parameter value from the parameter information is associated with a second combination of the set of different combinations of head orientation and torso orientation. The second combination is where the head orientation is supine and the torso orientation is non-supine. Further, a third parameter value from the parameter information is associated with a third combination of the set of different combinations of head orientation and torso orientation. The third combination is where the head orientation is non-supine and the torso orientation is supine. Further, a fourth parameter value from the parameter information is associated with a fourth combination of the set of different combinations of head orientation and torso orientation. The fourth combination is where the head orientation is non-supine and the torso orientation is non-supine.

In some embodiments, the instructions are configured to cause the processing circuitry to record, for use in the parameter information, the parameter value for each of the set of different combinations of head orientation and torso orientation. The recorded parameter value is established to reduce a likelihood of the subject experiencing a respiratory disturbance.

In some embodiments, the parameter value is established from a polysomnography, PSG, titration study conducted for each of the set of different combinations of head orientation and torso orientation.

In some embodiments, the parameter value is established by the respiratory support system. The respiratory support system is configured to determine the parameter value needed to reduce the likelihood of the subject experiencing the respiratory disturbance for each of the set of different combinations of head orientation and torso orientation. The respiratory support system is further configured to output the determined parameter value associated with each of the set of different combinations of head orientation and torso orientation for use in the parameter information.

In some embodiments, the instructions are configured to cause the processing circuitry to identify, from the indication, a change in the head orientation and/or torso orientation. In response to the change, the instructions are further configured to cause the processing circuitry to identify the parameter value of the therapy gas for the respiratory support system to use in supplying the therapy gas to the subject for the indicated change in the head orientation and/or torso combination based on the parameter information.

In some embodiments, the indication of a combination of the subject's head orientation and torso orientation is provided by at least one of: an orientation sensor of the sensing system; and/or an imaging device of the sensing system, wherein the imaging device is configured to image at least one of the subject's head and/or torso.

In some embodiments, the interface is further configured to receive an arousal indication produced by an arousal detection system operatively associated with the subject. The arousal detection system is configured to detect a change in sleep state of the subject and output the arousal indication in response to detecting the change. The instructions comprise further instructions to cause the processing circuitry to cause the respiratory support system to supply therapy gas with the parameter value at a default value in response to receiving the arousal indication. The further instructions are to cause the processing circuitry to vary the parameter value at a predefined rate until reaching the parameter value identified for the indicated combination of the subject's head orientation and torso orientation.

In a second aspect, a patient support system is described. The patient support system comprises the control system of any of the first aspect or related embodiments. The patient support system further comprises a respiratory support system for supplying therapy gas to the subject.

In a third aspect, a method is described. The method is a computer-implemented method. The method controls a respiratory support system for supplying therapy gas to a subject. The method comprises receiving an indication of a combination of the subject's head orientation and torso orientation. The indication is based on orientation data provided by a sensing system configured to detect the subject's head orientation and torso orientation. The method further comprises identifying a parameter value of the therapy gas for the respiratory support system to use in supplying the therapy gas to the subject for the indicated combination of the subject's head orientation and torso orientation. The parameter value is identified from parameter information associated with each of a set of different combinations of head orientation and torso orientation. The method further comprises causing the respiratory support system to supply the therapy gas with the identified parameter value.

In a fourth aspect, a non-transitory machine-readable medium is described. The non-transitory machine-readable medium stores instructions which, when executed by processing circuitry, cause the processing circuitry to implement the method of the third aspect.

Certain aspects or embodiments described herein may provide various technical improvements in terms of, for example, ensuring that the therapy gas provided by a respiratory support system meets a subject's respiratory needs, providing therapy gas in such a manner to increase subject comfort and/or compliance/adherence, and/or increasing the accuracy of determining a parameter value of therapy gas to supply to a subject. Further, subject comfort may be increased while reducing the risk of compromising therapy efficacy.

These and other aspects of the invention will be apparent from and elucidated with reference to the embodiment(s) described hereinafter.

BRIEF DESCRIPTION OF DRAWINGS

Exemplary embodiments of the invention will now be described, by way of example only, with reference to the following drawings, in which.

DETAILED DESCRIPTION OF THE EMBODIMENTS

Figure 1:
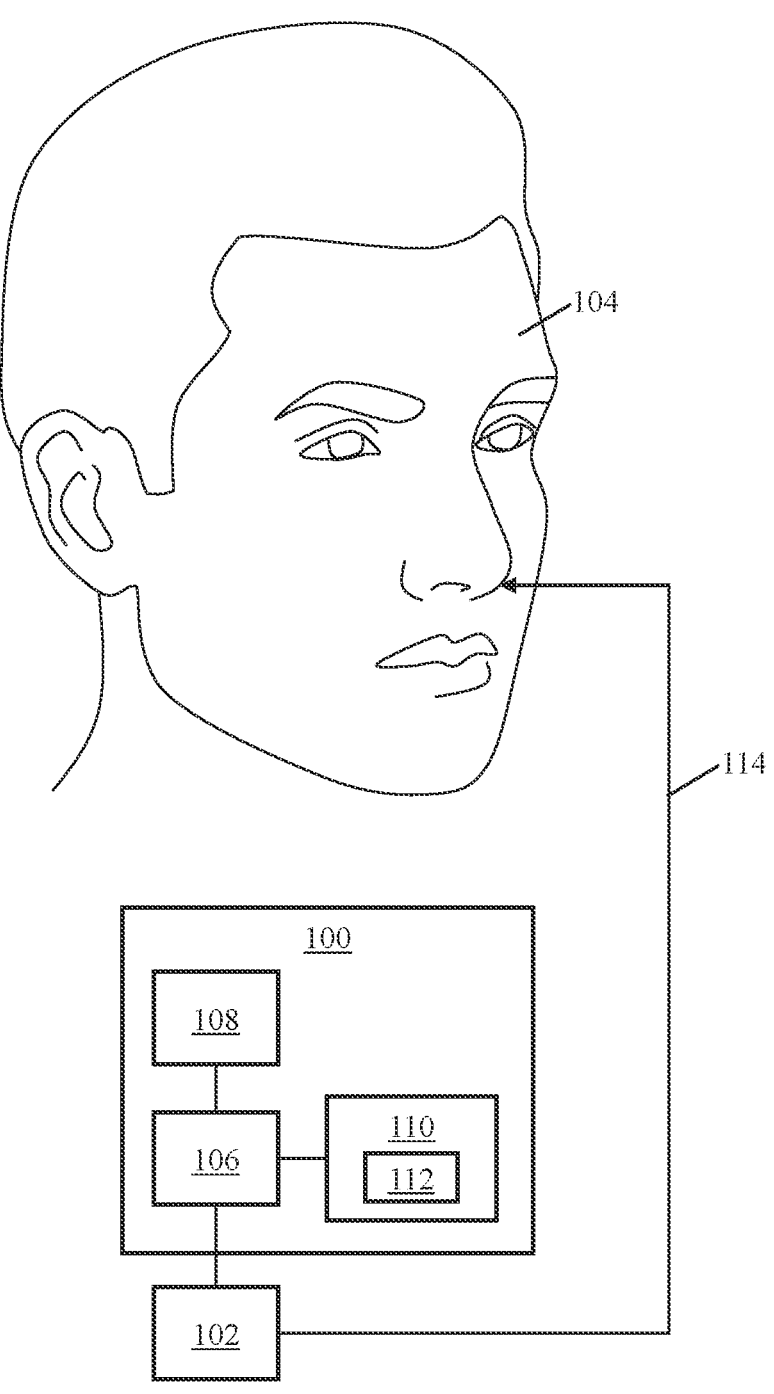
FIG. 1 is a schematic drawing of a control system for controlling a respiratory support system according to an embodiment.

As used herein, the term "respiratory support system" refers to a device for supplying therapy gas (such as air or gas with different proportions of constituent gases such as an enriched level of oxygen compared with air) to a subject such as a patient. Examples of different types of respiratory support systems include Positive Airway Pressure (PAP) systems such as Continuous PAP (CPAP) systems for providing therapy gas at a continuous pressure, Bi-level PAP (Bi-PAP) systems for providing therapy gas at two different pressures depending on whether the subject is inhaling or exhaling and Auto-PAP (APAP) systems for providing therapy gas at a pressure that varies over time depending on the subject's respiratory needs at the time (e.g., depending on sleep stage, medical needs, etc.). The type of respiratory support system recommended for a subject may depend on the subject's personal medical needs.

As used herein, the term "torso" (or "trunk") refers to the part of the body not including the head and limbs.

As used herein, the term "orientation" (or "position") refers to a directional relationship of a specified part of the body with respect to a rest surface such as a bed or couch upon which the body is positioned/resting (e.g., when sleeping). In the case of the "supine" orientation, a part of the body (e.g., the head and/or torso) may be on its back with respect to the rest surface such that the front of the body part is "facing" upwards, away from the rest surface. In the case of a "non-supine" orientation such as "side" or "lateral", a part of the body (e.g., the head and/or torso) may be on its side with respect to the rest surface such that the front and back of the body part is "facing" towards a lateral/side (i.e., left or right). In the case of another "non-supine" orientation such as "prone", a part of the body may be on its front with respect to the rest surface such that it is "facing" downwards, towards the rest surface. During sleep, a subject's body could adopt a variety of possible combinations of head and torso orientations. For example, the torso and head could both be in the supine orientation. In another example, the torso could be in the supine orientation while the head could be in the side orientation. In another example, the torso could be in the prone orientation while the head could be in the side orientation. Other torso and head orientation combinations may be possible for certain subjects. The torso and head orientation combinations that a subject adopts during sleep or rest may depend on factors such as the subject's preference, the subject's medical needs, the subject's anatomy, the type of rest surface (e.g., hard or soft mattress, inclination, etc.), involvement of medical equipment, etc.

Polysomnography (PSG) is an example type of sleep study to identify sleep issues in subjects. PSG may involve recording a subject's respiratory behavior during sleep and correlating such behavior with their body orientation since certain body orientations can cause respiratory disruptions for some subjects during their sleep.

The pressure settings of a respiratory support system used by a subject may be aligned to the therapeutic gas pressure in sleep that is determined during a PSG study conducted on the subject. To assure that there is an open airway for supine and non-supine orientations, the highest needed pressure is used in the respiratory support system settings. Since the severity of sleep apnea may be highest when the subject is in the supine orientation, the therapeutic pressure needed during sleep might not be optimal for routine use, e.g., in a home environment. Further, the lying position during a PSG study may be highly biased towards supine sleeping (e.g., due to the added burden of sensor cables, unfamiliarity with sleeping environment, etc.), which may contribute to a higher pressure being used for the subject (i.e., when sleeping in the non-supine position) than might otherwise be necessary.

Position-dependent OSA may be caused by certain anatomical structures that can be displaced by gravity (e.g., in a direction towards a rest surface). These anatomical structures include the soft palate, tongue and jawbone. All of these anatomical structures are located in the head, which means that an airway restriction/collapse may, in some cases, solely depend on the supine head position. There are no collapsible anatomical structures in the torso. However, if there is a heavy weight in the stomach region (e.g., in obese subjects), this weight may push up the subject's diaphragm when the subject is in supine position, which may cause a hypopnea event. A distinction may be made between hypoventilation caused by a narrowing of the airway, and a change in the lung volume, which may be compensated by hyperinflation in healthy subjects.

When the head moves from the supine to a lateral (side) orientation, the gravity related posterior (backwards) displacement of the tongue, jawbone and/or chin, may be reduced compared with when the head is in the supine orientation. Further, any bending of the neck may also influence airway obstructions. The occurrence and severity of airway obstructions may be reduced when either head, the torso, or both are in a lateral—instead of supine orientation.

In OSA subjects, the disease severity may correlate to the torso and head orientation. In OHS subjects, the disease severity may correlate to the torso orientation. In comorbid OSA and OHS subjects, head and torso orientation may contribute both to the respiration disturbance. Thus, the orientation of the head and/or torso may be a contributory factor to the severity of a particular respiratory condition.

Table 1 highlights some possible respiratory disturbances that may be observable in a subject for different orientation combinations of their torso and head.

TABLE 1

| Examples of respiratory disturbances observable in a subject while they sleep for the different orientations of the specified parts of their body (i.e., the head and torso orientations). Some orientation combinations may not be possible for certain subjects, or the subject may not regularly adopt such orientation combinations (e.g., denoted "x"). | | |
|---|---|---|
| Possible respiratory disturbance type? | Torso position: supine | Torso position: non-supine |
| Head position: supine | Apnea | x |
| Head position: side | Hypopnea | Hypopnea and/or apnea |

The physical effects of the head and torso being in different orientations may lead to certain respiratory disturbances such as apnea and hypopnea events, as indicated above. Different combinations of head and torso orientation may lead to different respiratory disturbances. While both the head and torso are in the supine orientation, apnea may typically be observed in some subjects due to the restriction of their airway caused by slippage of the jawbone, tongue, etc. In this case, a PAP system may deliver therapy gas to the subject at a high pressure to reduce the likelihood of the subject experiencing an apnea event.

In practice, this may mean that the therapy gas pressure might be overestimated in some cases, and when it is too high, it can cause an arousal (e.g., wake-up the subject or otherwise change the subject's sleep state). Further, the high pressure of the therapy gas might make it difficult to fall asleep when lying on those positions (e.g., head in a non-supine orientation). The burden of the high pressure may be cited as a reason for low patient compliance with CPAP systems. A similar situation may occur in patients using a BiPAP system. However, any type of respiratory support system may not recognize that the therapy gas supplied might not be optimal for the subject's sleep and/or therapy gas needs at a certain time.

Various embodiments described below may address at least one such issue and/or any other related issues as referred to herein.

FIG. 1 is a schematic drawing of a control system 100 for controlling a respiratory support system 102 for supplying therapy gas to a subject 104 according to an embodiment.

In some cases, the control system 100 could be implemented by a local computing system in the proximity of the subject 104 such as a dedicated computing system for implementing the functionality of the control system 100 and/or could be part of the respiratory support system 102 itself or other equipment associated with the subject 104. Although depicted as being distinct from the respiratory support system 102, in some cases, the functionality of the control system 100 could be provided by the respiratory support system 102 itself or other equipment (e.g., medical equipment) associated with the subject 104.

In some cases, the control system 100 could be implemented by a remote computing system such as a server (e.g., associated with a hospital, service provider, product manufacturer, etc.) or a cloud-based computing solution. In such cases, the control system 100 may be communicatively coupled to the respiratory support system 102 (and any other equipment or devices associated with the subject 104 for implementing the functionality of various embodiments described herein) for exchanging data (e.g., control data, measurements, etc.) therebetween.

The control system 100 comprises processing circuitry 106 (e.g., at least one processor) communicatively coupled to an interface 108 for receiving an indication of a combination of the subject's head orientation and torso orientation. As described in more detail below, the indication is based on orientation data provided by a sensing system configured to detect the subject's head orientation and torso orientation.

The "indication" may be in any appropriate format (e.g., raw data from an orientation detection system (not shown, discussed below), a bit indicator associated with each of the head orientation and torso orientation (e.g., "1" may mean supine while "0" may mean non-supine, etc.), characters or text that indicate the orientation, etc.) that can be understood or analyzed by the control system 100 in order to ascertain the combination of the subject's head orientation and torso orientation for the purpose of implementing the functionality described below. In other words, the indication provides the control system 100 with the needed information on the subject's (present or last measured/detected) head orientation and torso orientation. The indication may indicate one or both of the head orientation and/or torso orientation at any time (e.g., periodically or in response to a request, etc.). For example, a change in head or torso orientation may be indicated while, if no change in the other of the head or torso orientation has occurred, this may or may not be indicated.

The "interface" 108 may be communicatively coupled to the orientation detection system mentioned above and referred to elsewhere herein. The interface 108 may comprise any communications interface (e.g., a wireless or wired interface associated with any standard such as universal serial bus, Wi-Fi, Bluetooth, radio access (e.g., 3G, 4G, 5G), etc.) for exchanging data (e.g., control data, measurements, etc.) with the orientation detection system and/or the respiratory support system 102.

The control system 100 comprises a machine-readable medium 110 (e.g., non-transitory or any other type of memory device that can store information for any appropriate amount of time for use by the processing circuitry 106). The machine-readable medium 110 stores instructions 112 which, when executed by the processing circuitry 106, cause the processing circuitry 106 to identify a parameter value of the therapy gas for the respiratory support system 102 to use in supplying 114 the therapy gas to the subject 104 for the indicated combination of the subject's head orientation and torso orientation (i.e., indicated by the "indication"). The parameter value is identified from "parameter information" associated with each of a set of different combinations of head orientation and torso orientation.

The parameter information may comprise information on which parameter value(s) to use (i.e., need to be supplied) for the subject 104 based on an understanding of the subject's sleep and/or oxygen needs for different orientation combinations. Various embodiments described herein refer to how such an understanding is gained. The parameter information may be stored in a memory (such as the machine-readable medium 110 itself or another memory device accessible to the processing circuitry 106). In some cases, the parameter information could be stored in a database format that can implement a lookup table where each combination of head orientation and torso orientation is associated with a parameter value (or range of parameter values) to be used for the subject 104 if the subject's head and torso is oriented with such an orientation combination.

The instructions 112 further cause the processing circuitry 106 to cause the respiratory support system 102 to supply the therapy gas with the identified parameter value.

Thus, the parameter information comprises the parameter value to be identified by the control system 100 for each possible combination of head orientation and torso orientation. A different parameter value may be appropriate for each possible combination. Thus, in response to the control system 100 identifying that a certain parameter value is to be used for the indicated combination of head orientation and torso orientation, such a parameter value may be indicated to the respiratory support system 102 (e.g., via a control signal or some other indication), to cause the respiratory support system 102 to deliver the therapy gas to the subject with the identified parameter value.

By way of example, a subgroup of OSA subjects have position-dependent OSA (POSA), which may be defined as a difference of 50% or more in apnea index between supine and non-supine orientations. For a subgroup of these subjects, it seems that head orientation, separately from torso orientation, is an additional factor for the occurrence of apnea in OSA subjects. For example, the therapeutic PAP pressure (which is an example of a "parameter") needed for when the subject's head is in the supine orientation is higher than when the subject's head is in the lateral orientation (i.e., the "parameter value" may need to be indicated as being higher when the subject's head is in the supine orientation).

Similar considerations may apply to subjects with other conditions such as OHS where the head orientation may, in addition to torso orientation, be a factor worth considering when determining how much PAP pressure (or another parameter value) to supply.

Certain embodiments described herein (including the control system 100) may use a detected head and body orientation during (e.g., PAP) therapy to identify the parameter value (e.g., PAP pressure) based on the detected orientation combination. Further, certain embodiments described herein may help to ensure that the therapy gas provided by the respiratory support system 102 meets a subject's respiratory needs (e.g., sufficient oxygen delivery/ensuring airway remains unobstructed), provide therapy gas in such a manner to increase subject comfort and/or compliance/adherence to the therapy and/or increase the accuracy of determining a parameter value of therapy gas to supply to a subject 104. Further, subject comfort may be increased (e.g., by reducing the pressure of the therapy gas) while reducing the risk of compromising therapy efficacy (e.g., by avoiding the pressure of the therapy gas dropping below an acceptable threshold for the subject 104).

In a possible implementation, a preset/default/predetermined therapy pressure may be needed for a subject if they adopt the supine head orientation (in combination with the torso being in the supine or non-supine orientation). However, if the subject adopts a non-supine head position (in combination with the torso being in the supine or non-supine orientation), the parameter value(s) to be used instead of the preset/default may have (e.g., also) been determined during a modified PSG titration procedure. Where a PSG titration has not been performed (e.g., where an auto-PAP system is used), the parameter value(s) could be ascertained e.g., during a modified auto-PAP procedure which makes use of the same principle (e.g., indicating the orientation combination and correlating this indication with the needed parameter value for each possible orientation combination). In some cases, CPAP and BiPAP devices can then be programmed to provide an appropriate therapy gas pressure for each combination of head and torso orientation.

Thus, in some cases, the "parameter information" may have been previously determined for the subject (e.g., using measurements during a modified MSG titration procedure or using a modified auto-PAP procedure). In use of the control system 100, the orientation combination may be indicated to the control system 100, which then controls the respiratory support system 102 to supply therapy gas with the parameter value specified by the parameter information for the indicated combination of head orientation and torso orientation.

Figure 2:
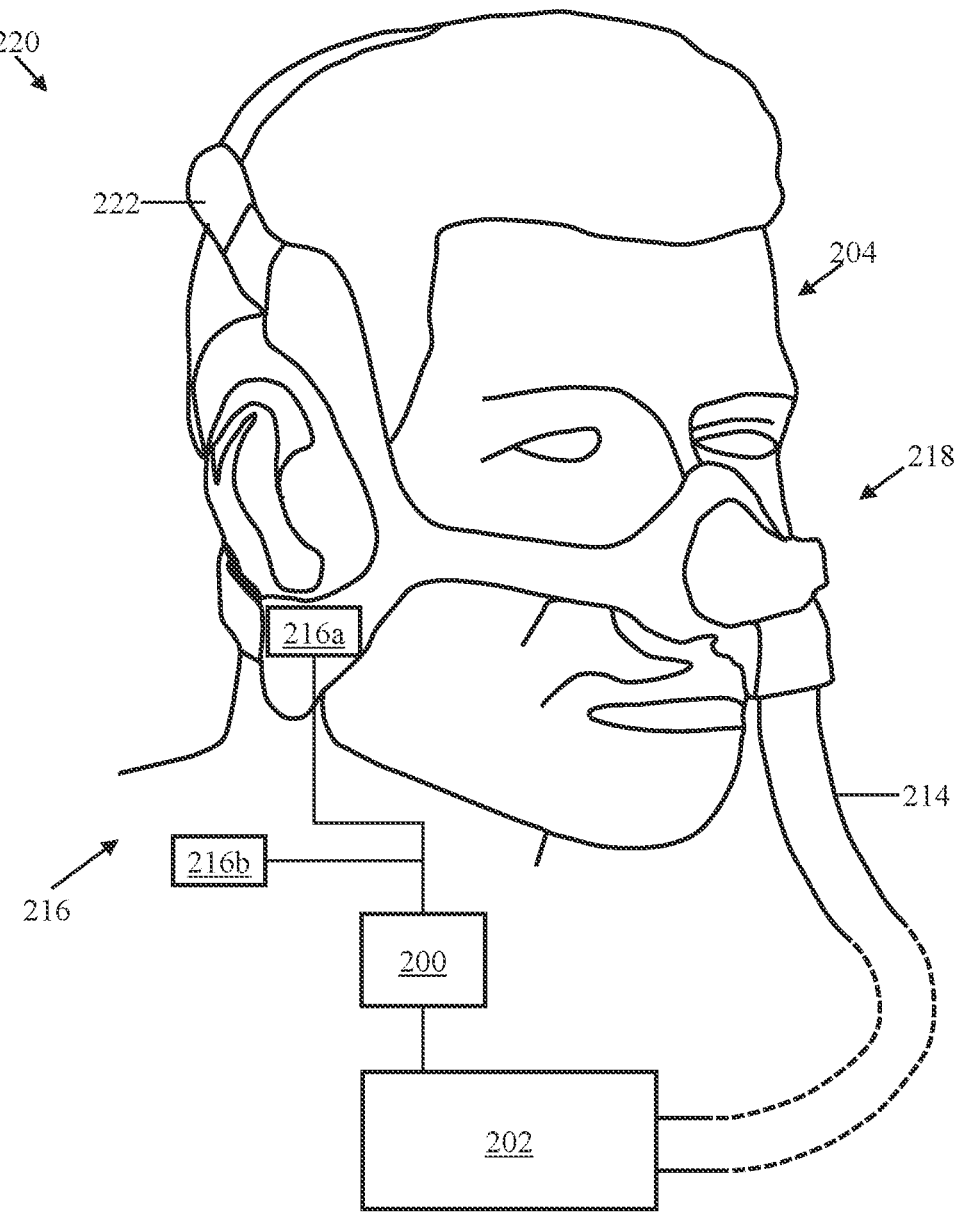
FIG. 2 is a schematic drawing of a patient support system according to an embodiment.

FIG. 2 is a schematic drawing of a patient support system 220 according to an embodiment. Reference signs for features like or to similar to features shown and described in relation to FIG. 1 are incremented by 100 compared with the corresponding features in FIG. 1. Certain features of the patient support system 220, as described below, may be omitted or modified in some embodiments.

The patient support system 220 comprises a control system 200. The control system 200 may implement the functionality of the control system 100 or any related embodiment.

The patient support system 220 further comprises a respiratory support system 202 for supplying therapy gas to the subject 204. The respiratory support system 202 may implement the functionality of the respiratory support system 102 or any related embodiment.

The patient support system 220 further comprises a sensing system 216 (in this embodiment, comprising a first sensor 216a and a second sensor 216b) for performing measurements/sensing to facilitate detecting the orientation of the subject's head and torso. The sensing system 216 is communicatively coupled to the control system 200 (e.g., the interface 108 thereof) so that orientation data generated by the sensing system 216 can be received by the control system 200. Such orientation data may indicate the orientation of the subject's head (e.g., orientation data from the first sensor 216a) and the orientation of the subject's torso (e.g., orientation data from the second sensor 216b). Thus, in some cases, the "orientation data" is useable as the "indication" referred to in relation to the control system 100 and other embodiments. The sensing system 216 may detect the subject's head orientation based on a measurement of a position of at least part of the subject's head. Such a measurement yields the orientation data described above. The sensing system 216 may detect the subject's torso orientation based on a measurement of a position of at least part of the subject's torso. Such a measurement may indicate the position of the part of the subject's head and/or torso relative to a spatial point of reference such that this measurement is indicative of the overall orientation of the head and/or torso. In other words, the measurement may be a direct measurement of the head and/or torso orientation. Use of such a direct measurement may be more accurate than making an inference about the subject's orientation based on an indirect measurement of another parameter that does not directly indicate the subject's position/orientation relative to a spatial point of reference. Examples of the sensing system 216 are given below.

The nature of the orientation data may depend on the type of sensing system 216 used. In this embodiment, the sensing system 216 comprises a (first) position/movement sensor 216a associated with the head (e.g., attached to the head itself or another article such as clothing or medical equipment) and a (second) position/movement sensor 216b associated with the torso (e.g., attached to the torso itself or another article such as clothing or medical equipment). Such position/movement sensors may be based on accelerometers that detect movement/a change of inclination that is indicative of orientation.

Another type of sensing system 216 may be a pressure pad (positioned under the subject 204) configured to detect (e.g., a change in) a spatial pressure profile indicative of the subject's head and/or torso orientation. For example, the back of the head/torso (corresponding to the supine orientation) may have a different spatial pressure profile to the side/front of the head/torso (corresponding to the non-supine orientation). Thus, the sensing system 216 may not necessarily be physically coupled to the subject 204, their clothing or any medical equipment such as a mask associated with the subject 204. The output of such a pressure pad may represent "orientation data".

In some embodiments, the sensing system 216 may comprise an imaging system (e.g., a camera, not shown) for imaging the subject 204. The image data (which represents "visual" orientation data) produced by the imaging system can be analyzed (e.g., by an artificial intelligence (AI) model such as a neural network) to determine the orientation. An example may be a face detection model where, if a face is detected by a camera above the rest surface, this may indicate that the subject's head is in the supine orientation.

Otherwise, if no face is detected, the subject 204 is in a non-supine orientation. Other (AI or non-AI) models may be possible, providing the model is configured (e.g., trained or set-up) appropriately for the scenario (e.g., position of the imaging system with respect to the subject 204, visible parts of the subject's body, etc.).

In some embodiments, the sensing system 216 may comprise an ultrasound or radar-based system mounted in the vicinity of the subject 204 and configured to detect the orientation of the head and/or torso (or a change thereof).

In some implementations of the patient support system 220, a direct detection/measurement of the subject's orientation (as in the previous description) may not be needed to determine the orientation of the head and torso. Instead, other medical equipment such as the respiratory support system 202 itself may acquire data during monitoring (such as a respiration pattern or a change thereof) which may indicate the subject's orientation. An analysis of such monitoring data may provide an indication of the orientation. For example, a flow analysis of the therapy gas may be correlated with the subject's head and torso orientation based on a previous study of the subject's respiratory behavior when sleeping in different orientation combinations. However, the flow of therapy gas is an example of a parameter that does not directly indicate the subject's position/orientation relative to a spatial point of reference.

The sensing system 216 may provide the "indication" directly or indirectly. For example, the "indication" may comprise raw "orientation data" generated by the sensing system 216 itself (which can be analyzed by the control system 200). In another example, the "indication" may comprise transformed data generated by the sensing system 216 itself or another entity such as an orientation detection system (not shown but could be implemented by the control system 200 itself) configured to identify the subject's head orientation and torso orientation based on the raw data generated by the sensing system 216, transform such raw data and output the "indication" of the combination of the subject's head orientation and torso orientation for receipt by the interface 108.

As depicted by FIG. 2, the respiratory support system 202 supplies the therapy gas to the subject 204 via a gas supply hose 214 (e.g., flexible tubing) coupled to a subject interface 218 associated with the subject 204. In this case, the subject interface 218 comprises a nasal mask (for supplying the therapy gas to the subject's nose) that is attached to the subject's head via a mounting device 222 such as a set of adjustable straps extending around the subject's head. However, in other cases, the subject interface 218 could comprise a different type of subject interface 218 such as an oronasal mask.

Some possible implementations of the patient support system 220 are now described according to various embodiments.

In an implementation, the patient support system 220 is calibrated with at least two different sets of therapeutic pressures (or pressure ranges), depending on the different torso and head orientations. When the subject 204 is lying in supine head and torso orientation, it uses the default range. Upon identifying that the subject's head has been repositioned to change its orientation, the control system 200 adopts the parameter value range for the non-supine orientation (usually a lower pressure), based on the "parameter information".

In an implementation, the first sensor 216a may be in the form of an accelerometer (or other orientation sensor) integrated in the subject interface 218 or otherwise physically associated with the head for providing the orientation data regarding the head orientation. An additional accelerometer (or other orientation sensor) associated with the second sensor 216*b* may be mounted to, coupled to or otherwise physically associated with the torso for providing the orientation data regarding the torso orientation. Both sensors 216*a*, 216*b* may be connected either with a cable, or wirelessly, to the control system 200, which may control a parameter such as the pressure of therapy gas delivered to the subject 204 based on the detected head and torso orientation.

In an implementation, the orientation-dependent therapeutic pressures can be determined during a PSG titration study using orientation data collected by the sensing system 216 (e.g., the same sensing system 216 used by the subject 204 or a different sensing system 216 to the one used by the subject 204). As explained above, the sensing system 216 may be configured to determine whether the orientation corresponds to, for example: a non-supine head and supine torso orientation (i.e., $H_{NS}+T_S$), both a supine head and supine torso orientation (i.e., $H_S+T_S$), a supine head and non-supine torso orientation (i.e., $H_S T_{NS}$), or both a non-supine head and non-supine torso orientation (i.e., $H_{NS}+T_{NS}$). Each of $H_{NS}+T_S$, $H_S+T_S$, $H_S+T_{NS}$ and $H_{NS}+T_{NS}$ refers to an "orientation combination".

In an implementation, the pressure of the therapy gas for each of these orientation combinations may be determined via a PSG titration study or other data regarding appropriate pressure for each of the orientation combinations. Where the respiratory support system 202 is in the form of a CPAP or BiPAP system, the pressure of the supplied therapy gas may correspond to the parameter value indicated by the control system 200.

For example, when the $H_S+T_S$ orientation combination is indicated, the respiratory support system 202 may provide therapy gas at the titrated pressure needed to clear obstructions, which may correspond to the highest therapeutic pressure to be provided by the respiratory support system 202.

When the $H_{NS}+T_{NS}$ orientation combination is indicated, respiratory support system 202 may provide therapy gas at the titrated pressure needed to clear obstructions, which may correspond to the lowest pressure to be provided by the respiratory support system 202.

When the $H_{NS}+T_S$ or $H_S+T_{NS}$ orientation combination is indicated, respiratory support system 202 may provide the titrated pressure needed to clear obstructions, which may correspond to an intermediate pressure between the highest and lowest pressure.

In an implementation, the therapeutic pressure can be automatically determined with a respiratory support system 202 implementing auto-PAP. Instead of a manual titration session such as may be performed by skilled nursing staff, the respiratory support system 202 uses the measured AHI to determine the minimum therapeutic pressure. However, in this implementation the auto-PAP procedure may be modified such that the head and torso orientation combination is taken into account. For example, the auto-PAP titration procedure may be performed separately for each torso/head orientation combination.

In an implementation, a protocol for the auto-PAP device settings may be provided for each orientation combination. For the $H_S+T_S$ orientation combination, a first part of the protocol provides pressure for airway clearance and to overcome apnea events. For the $H_{NS}+T_S$ or $H_S+T_{NS}$ orientation combination, a second part of the protocol provides pressure to overcome hypoventilation. For the $H_{NS}+T_{NS}$ orientation combination, a third part of the protocol provides pressure to balance the tidal volume/minute volume.

In an implementation, the orientation of the head may be detected and used to determine the parameter value, based on a titration study that also correlates measurements with the head orientation. Thus, the intervention may be restricted to adjustments of the therapy gas pressure to the effect of only head changes.

In an implementation, the control system 200 may be able to detect an arousal. In case of an arousal (e.g., a wake-up event) the pressure may reset to the start value. After reset the pressure may be slowly varied (e.g., ramped up to a predefined holding pressure). A slow ramping up may make it easier for the subject to fall asleep again.

Some further embodiments relating to the above are now described.

In some embodiments, the parameter value to use is established, for each of the set of different combinations of head orientation and torso orientation, to reduce a likelihood of the subject experiencing a respiratory disturbance (e.g., a sleep apnea event, hypopnea event, wake-up event, etc.).

In some embodiments, the parameter information comprises a range of parameter values to use, for each of the set of different combinations of head orientation and torso orientation, to reduce the likelihood of the subject experiencing the respiratory disturbance. In some cases, the range may refer to a lower and upper parameter value. In some cases, the range may refer to a minimum (threshold) parameter value to use. In some cases, the range may refer to a maximum parameter value to use.

In some embodiments, the instructions (e.g., instructions 112) are configured to cause the processing circuitry 106 to record, for use in the parameter information, the parameter value established to reduce the likelihood of the subject 204 experiencing the respiratory disturbance for each of the set of different combinations of head orientation and torso orientation. Thus, such embodiments refer to studies that establish what parameter values may be suitable for reducing the likelihood of the subject experiencing the respiratory disturbance when in each of the possible orientation combinations. Thus, the recorded values may be stored as part of the "parameter information".

In some embodiments, the parameter value is established from a polysomnography, PSG, titration study conducted for each of the set of different combinations of head orientation and torso orientation.

In some embodiments, the parameter value is established by the respiratory support system 202. In such embodiments, the respiratory support system 202 (such as an auto-PAP system) may be configured to determine the parameter value needed to reduce the likelihood of the subject 204 experiencing the respiratory disturbance for each of the set of different combinations of head orientation and torso orientation. The respiratory support system 202 may further be configured to output the determined parameter value associated with each of the set of different combinations of head orientation and torso orientation for use in the parameter information.

In some embodiments, the instructions (e.g., instructions 112) are configured to cause the processing circuitry 106 to identify, from the indication, a change in the head orientation and/or torso orientation. In response to the change, processing circuitry 106 may be caused to identify the parameter value of the therapy gas for the respiratory support system 202 to use in supplying the therapy gas to the subject for the indicated change in the head orientation and/or torso combination based on the parameter information. In such embodiments, where a change in orientation is detected, the parameter information may be checked to see if a change in parameter value is needed. If so, such a change may be indicated to the respiratory support system 202.

In some embodiments, the indication is configured to indicate whether the subject's head orientation and torso orientation are the same or different. In an example, the head orientation and torso orientation may be the same if both orientations are supine or both orientations are non-supine. In a further example, the head orientation and torso orientation may be the same if both orientations are one of the non-supine orientations such as side or prone. In a further example, the head orientation and torso orientation may be different if one of the orientations is supine and the other of the orientations is non-supine. In a further example, the head orientation and torso orientation may be different if one of the orientations is one of the non-supine orientations (e.g., side) and the other of the orientations is the other of the non-supine orientations (e.g., prone).

In some embodiments, the indication comprises information (e.g., information on the subject's present or last measured/detected head orientation and torso orientation) indicative of the subject's head orientation being different to the subject's torso orientation.

In some embodiments, the head orientation is one of: a supine head orientation or non-supine head orientation. Further, the torso orientation is one of: a supine torso orientation or non-supine torso orientation.

In some embodiments, the parameter value to use is a default parameter value when the indicated combination comprises the supine head orientation and the supine torso orientation. The parameter value to use is different to the default parameter value when the indicated combination comprises at least one of: a non-supine head orientation and/or non-supine torso orientation. For example, the default parameter value may be an upper pressure value to use when the subject's head and torso are in the supine orientation. The parameter value to be used may be different when the head and/or torso is in the non-supine orientation.

In some embodiments, a first parameter value from the parameter information is associated with a first combination of the set of different combinations of head orientation and torso orientation. The first combination is where the head orientation is supine and the torso orientation is supine. Further, a second parameter value from the parameter information is associated with a second combination of the set of different combinations of head orientation and torso orientation. The second combination is where the head orientation is supine and the torso orientation is non-supine. Further, a third parameter value from the parameter information is associated with a third combination of the set of different combinations of head orientation and torso orientation. The third combination is where the head orientation is non-supine and the torso orientation is supine. Further, a fourth parameter value from the parameter information is associated with a fourth combination of the set of different combinations of head orientation and torso orientation. The fourth combination is where the head orientation is non-supine and the torso orientation is non-supine.

In some embodiments, the parameter value is at least one of: a pressure value of the therapy gas; and/or an oxygen level of the therapy gas. In the latter case, the respiratory support system 202 may deliver therapy gas with a specified proportion of constituent gases (e.g., enriched oxygen) in response to the indicated orientation combination. For example, if therapy gas pressure cannot be varied in some circumstances, the oxygen level may be changed instead.

In some embodiments, the indication of a combination of the subject's head orientation and torso orientation is provided by a sensing system 216 in the form of an orientation sensor configured to detect the subject's head orientation and/or torso orientation. The orientation sensor could be: a position/movement sensor (e.g., accelerometer) physically associated with the subject's head, a position/movement sensor physically associated with the subject's torso, a pressure pad positioned under the subject's head, a pressure pad positioned under the subject's torso, etc. The physical association may refer to being physically coupled to or otherwise in physical contact with part of the subject's head and/or torso to detect movement/the orientation thereof.

In some implementations, the indication of a combination of the subject's head orientation and torso orientation is provided by the respiratory support system 202 via a flow analysis of the therapy gas supplied by the respiratory support system 202.

In some embodiments, the indication of a combination of the subject's head orientation and torso orientation is provided by a sensing system 216 in the form of an imaging device (not shown but schematically represented by the sensing system 216) configured to image at least one of the subject's head and/or torso. In some cases, the sensing system 216 may be in the form of a non-contact sensor such as an ultrasound or radar system, etc.

In some embodiments, the interface 108 is further configured to receive an arousal indication produced by an arousal detection system (e.g., implemented by the sensing system 216 or by a respiratory monitoring function of the respiratory support system 202 itself) operatively associated with the subject 204. The arousal detection system is configured to detect a change in sleep state of the subject 204 and output the arousal indication in response to detecting the change. The instructions 112 may comprise further instructions to cause the processing circuitry 106 to cause the respiratory support system 202 to supply therapy gas with the parameter value at a default value in response to receiving the arousal indication. However, such further instructions may further cause the respiratory support system 202 to vary the parameter value at a predefined rate until reaching the parameter value identified for the indicated combination of the subject's head orientation and torso orientation. Such varying may refer to "ramping" the parameter value (e.g., pressure).

Figure 3:
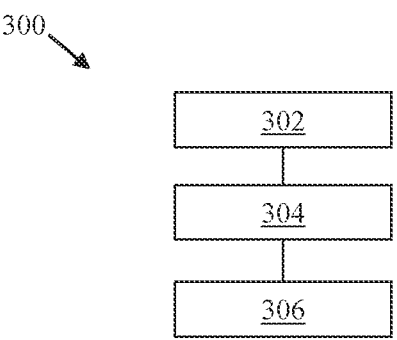
FIG. 3 refers to a method of controlling a respiratory support system according to an embodiment.

FIG. 3 refers to a method 300 of controlling a respiratory support system 102 for supplying therapy gas to a subject 104 according to an embodiment. The method 300 may be implemented by the control system 100, 200 of FIG. 1 or 2. The method 300 is a computer-implemented method. In FIG. 3, the method 300 may implement the functionality of the control system 100 of FIG. 1 and therefore reference is made to FIG. 1 in the description of the method 300.

The method 300 comprises, at block 302, receiving an indication of a combination of the subject's head orientation and torso orientation. The indication is based on orientation data provided by the sensing system 216, which may be configured to detect the subject's head orientation and torso orientation.

The method 300 further comprises, at block 304, identifying a parameter value of the therapy gas for the respiratory support system 102 to use in supplying the therapy gas to the subject for the indicated combination of the subject's head orientation and torso orientation. The parameter value is identified from parameter information associated with each of a set of different combinations of head orientation and torso orientation.

The method 300 further comprises, at block 306, causing the respiratory support system 102 to supply the therapy gas with the identified parameter value.

Further methods may be based on the functionality described above in relation to FIGS. 1 and 2, and the related implementations/embodiments. In such cases, further blocks may be implementable as computer-implemented methods to be implemented by the control system 100, 200.

Figure 4:
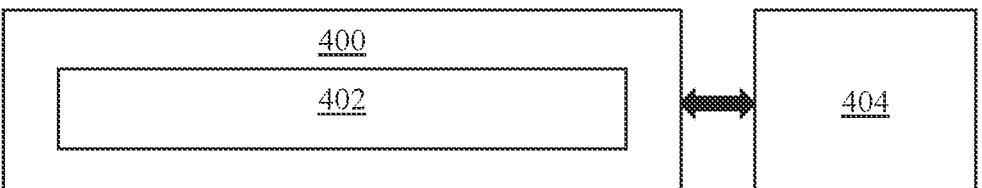
FIG. 4 is a schematic drawing of a machine-readable medium for implementing various embodiments.

FIG. 4 is a schematic drawing of a non-transitory machine-readable medium 400 for implementing the functionality of certain embodiments described herein. For example, certain functionality of the control system 100, 200 of FIGS. 1 and 2, the method 300, or related embodiments may be implemented by the machine-readable medium 400. The machine-readable medium 400 stores instructions 402 which, when executed by processing circuitry 404, cause the processing circuitry 404 to implement such functionality.

In one implementation, the instructions 402 cause the processing circuitry 404 to implement the method 300. In some related implementations, the instructions 402 cause the processing circuitry 404 to implement methods corresponding to the functionality of any embodiment relating to the control system 100, 200.

Figure 5:
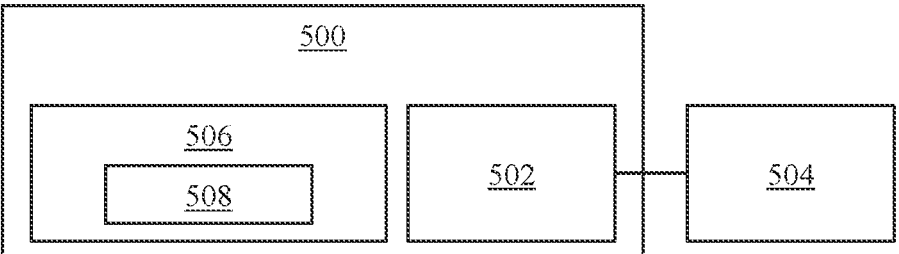
FIG. 5 is a schematic drawing of apparatus for implementing various embodiments.

FIG. 5 is a schematic drawing of apparatus 500 for implementing functionality of certain embodiments described herein. For example, certain functionality of the control system 100, 200 of FIGS. 1 and 2, the method 300, or related embodiments may be implemented by the apparatus 500.

The apparatus 500 comprises processing circuitry 502. The processing circuitry 502 is configured to communicate with an interface 504. The interface 504 may be any interface (wireless or wired) implementing a communications protocol to facilitate exchange of data with other devices such as the sensing system 316 and/or respiratory support system 102, 202.

The apparatus 500 further comprises a machine-readable medium 506 (e.g., non-transitory or otherwise) storing instructions 508 which, when executed by the processing circuitry 502, cause the processing circuitry 502 to implement the abovementioned functionality of certain embodiments described herein.

In one implementation, the instructions 508 cause the processing circuitry 502 to implement the method 300. In some related implementations, the instructions 508 cause the processing circuitry 502 to implement methods corresponding to the functionality of any embodiment relating to the control system 100, 200.

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment.

This disclosure includes the subject-matter set out by the following numbered paragraphs:

1. A control system for controlling a respiratory support system for supplying therapy gas to a subject, the control system comprising:

processing circuitry communicatively coupled to an interface for receiving an indication of a combination of the subject's head orientation and torso orientation; and a machine-readable medium storing instructions which, when executed by the processing circuitry, cause the processing circuitry to:

identify, from parameter information associated with each of a set of different combinations of head orientation and torso orientation, a parameter value of the therapy gas for the respiratory supply system to use in supplying the therapy gas to the subject for the indicated combination of the subject's head orientation and torso orientation; and cause the respiratory support system to supply the therapy gas with the identified parameter value.

2. The control system of paragraph 1, wherein the parameter value to use is established, for each of the set of different combinations of head orientation and torso orientation, to reduce a likelihood of the subject experiencing a respiratory disturbance.

3. The control system of paragraph 2, wherein the parameter information comprises a range of parameter values to use, for each of the set of different combinations of head orientation and torso orientation, to reduce the likelihood of the subject experiencing the respiratory disturbance.

4. The control system of any of paragraphs 2 to 3, wherein the instructions are configured to cause the processing circuitry to record, for use in the parameter information, the parameter value established to reduce the likelihood the subject experiencing the respiratory disturbance for each of the set of different combinations of head orientation and torso orientation.

5. The control system of paragraph 4, wherein the parameter value is established from a polysomnography, PSG, titration study conducted for each of the set of different combinations of head orientation and torso orientation.

6. The control system of paragraph 4, wherein the parameter value is established by the respiratory support system, wherein the respiratory support system is configured to: determine the parameter value needed to reduce the likelihood of the subject experiencing the respiratory disturbance for each of the set of different combinations of head orientation and torso orientation; and output the determined parameter value associated with each of the set of different combinations of head orientation and torso orientation for use in the parameter information.

7. The control system of any of paragraphs 1 to 6, wherein the instructions are configured to cause the processing circuitry to:

identify, from the indication, a change in the head orientation and/or torso orientation; and in response to the change, identify the parameter value of the therapy gas for the respiratory supply system to use in supplying the therapy gas to the subject for the indicated change in the head orientation and/or torso combination based on the parameter information.

8. The control system of any of paragraphs 1 to 7, wherein the head orientation is one of: a supine head orientation or non-supine head orientation, and wherein the torso orientation is one of: a supine torso orientation or non-supine torso orientation.

9. The control system of paragraph 8, wherein the parameter value to use is a default parameter value when the indicated combination comprises the supine head orientation and the supine torso orientation, and wherein the parameter value to use is different to the default parameter value when the indicated combination comprises at least one of: a non-supine head orientation and/or non-supine torso orientation.

10. The control system of any of paragraphs 1 to 9, wherein the parameter value is at least one of:

a pressure value of the therapy gas; and/or an oxygen level of the therapy gas.

11. The control system of any of paragraphs 1 to 10, wherein the indication of a combination of the subject's head orientation and torso orientation is provided by at least one of:

an orientation sensor configured to detect the subject's head orientation and/or torso orientation;

the respiratory support system via a flow analysis of the therapy gas supplied by the respiratory support system; and/or an imaging device configured to image at least one of the subject's head and/or torso.

12. The control system of any of paragraphs 1 to 11, wherein the interface is further configured to receive an arousal indication produced by an arousal detection system operatively associated with the subject, wherein the arousal detection system is configured to detect a change in sleep state of the subject and output the arousal indication in response to detecting the change, and wherein the instructions comprise further instructions to cause the processing circuitry to:

cause the respiratory support system to supply therapy gas with the parameter value at a default value in response to receiving the arousal indication; and vary the parameter value at a predefined rate until reaching the parameter value identified for the indicated combination of the subject's head orientation and torso orientation.

13. A patient support system, comprising:

the control system of any of paragraphs 1 to 12;

a respiratory support system for supplying therapy gas to the subject.

14. A computer-implemented method of controlling a respiratory support system for supplying therapy gas to a subject, the method comprising:

receiving an indication of a combination of the subject's head orientation and torso orientation;

identifying, from parameter information associated with each of a set of different combinations of head orientation and torso orientation, a parameter value of the therapy gas for the respiratory supply system to use in supplying the therapy gas to the subject for the indicated combination of the subject's head orientation and torso orientation; and causing the respiratory support system to supply the therapy gas with the identified parameter value 15. A non-transitory machine-readable medium storing instructions which, when executed by processing circuitry, cause the processing circuitry to implement the method of paragraph 14.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, flash storage, etc.) having computer readable program codes therein or thereon.

The present disclosure is described with reference to flow charts and block diagrams of the method, devices, and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine-readable instructions may, for example, be executed by a general-purpose computer, a special purpose computer, an embedded processor, or processors of other programmable data processing devices to realize the functions described in the description and diagrams. In particular, a processor or processing circuitry, or a module thereof, may execute the machine-readable instructions. Thus, functional modules of apparatus and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine-readable instructions may also be stored in a computer readable storage that can guide the computer or other programmable data processing devices to operate in a specific mode.

Such machine-readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems.

The invention claimed is:

1. A control system for controlling a respiratory support system for supplying therapy gas to a subject, the control system comprising:

processing circuitry communicatively coupled to an interface for receiving an indication of a combination of the subject's head orientation and torso orientation, wherein the indication is based on orientation data provided by a sensing system configured to detect the subject's head orientation and torso orientation;

wherein the interface is further configured to receive an arousal indication and a machine-readable medium storing instructions which, when executed by the processing circuitry, cause the processing circuitry to:

identify, from parameter information associated with each of a set of different combinations of head orientation and torso orientation, a parameter value of the therapy gas for the respiratory support system to use in supplying the therapy gas to the subject for the indicated combination of the subject's head orientation and torso orientation; and cause the respiratory support system to supply the therapy gas with the identified parameter value; and in response to receiving the arousal indication, cause the respiratory support system to supply therapy gas with the parameter value at a default value, and vary the parameter value at a predefined rate until reaching the parameter value identified for the indicated combination of the subject's head orientation and torso orientation.

2. The control system of claim 1, wherein the indication is configured to indicate whether the subject's head orientation and torso orientation are the same or different.

3. The control system of claim 1, wherein the indication comprises information indicative of the subject's head orientation being different to the subject's torso orientation.

4. The control system of claim 1, wherein the head orientation is one of: a supine head orientation or non-supine head orientation, wherein the torso orientation is one of: a supine torso orientation or non-supine torso orientation.

5. The control system of claim 4, wherein the parameter value to use is a default parameter value when the indicated combination comprises the supine head orientation and the supine torso orientation, and wherein the parameter value to use is different to the default parameter value when the indicated combination comprises at least one of: a non-supine head orientation and/or non-supine torso orientation.

6. The control system of claim 1, wherein: a first parameter value from the parameter information is associated with a first combination of the set of different combinations of head orientation and torso orientation, wherein the first combination is where the head orientation is supine and the torso orientation is supine; a second parameter value from the parameter information is associated with a second combination of the set of different combinations of head orientation and torso orientation, wherein the second combination is where the head orientation is supine and the torso orientation is non-supine; a third parameter value from the parameter information is associated with a third combination of the set of different combinations of head orientation and torso orientation, wherein the third combination is where the head orientation is non-supine and the torso orientation is supine; and a fourth parameter value from the parameter information is associated with a fourth combination of the set of different combinations of head orientation and torso orientation, wherein the fourth combination is where the head orientation is non-supine and the torso orientation is non-supine.

7. The control system of claim 1, wherein the instructions are configured to cause the processing circuitry to record, for use in the parameter information, the parameter value for each of the set of different combinations of head orientation and torso orientation, wherein the recorded parameter value is established to reduce a likelihood of the subject experiencing a respiratory disturbance.

8. The control system of claim 7, wherein the parameter value is established from a polysomnography, PSG, titration study conducted for each of the set of different combinations of head orientation and torso orientation.

9. The control system of claim 7, wherein the parameter value is established by the respiratory support system, wherein the respiratory support system is configured to: determine the parameter value needed to reduce the likelihood of the subject experiencing the respiratory disturbance for each of the set of different combinations of head orientation and torso orientation; and output the determined parameter value associated with each of the set of different combinations of head orientation and torso orientation for use in the parameter information.

10. The control system of claim 1, wherein the instructions are configured to cause the processing circuitry to: identify, from the indication, a change in the head orientation and/or torso orientation; and in response to the change, identify the parameter value of the therapy gas for the respiratory support system to use in supplying the therapy gas to the subject for the indicated change in the head orientation and/or torso combination based on the parameter information.

11. The control system of claim 1, wherein the indication of a combination of the subject's head orientation and torso orientation is provided by at least one of: an orientation sensor of the sensing system; and/or an imaging device of the sensing system, wherein the image device is configured to image at least one of the subject's head and/or torso.

12. The control system of claim 1, wherein the interface is further configured to receive the arousal indication produced by an arousal detection system operatively associated with the subject, wherein the arousal detection system is configured to detect a change in sleep state of the subject and output the arousal indication in response to detecting the change.

13. A patient support system, comprising: the control system of claim 1; a respiratory support system for supplying therapy gas to the subject.

14. A computer-implemented method of controlling a respiratory support system for supplying therapy gas to a subject, the method comprising:

receiving an indication of a combination of the subject's head orientation and torso orientation, wherein the indication is based on orientation data provided by a sensing system configured to detect the subject's head orientation and torso orientation;

identifying, from parameter information associated with each of a set of different combinations of head orientation and torso orientation, a parameter value of the therapy gas for the respiratory support system to use in supplying the therapy gas to the subject for the indicated combination of the subject's head orientation and torso orientation;

and causing the respiratory support system to supply the therapy gas with the identified parameter value; and receiving an arousal indication; in response to receiving the arousal indication, causing the respiratory support system to supply therapy gas with the parameter value at a default value; and varying the parameter value at a predefined rate until reaching the parameter value identified for the indicated combination of the subject's head orientation and torso orientation.

15. A non-transitory machine-readable medium storing instructions which, when executed by processing circuitry, cause the processing circuitry to implement the method of claim 14.

* * * * *

5